United States Patent [19]

Manfredi

[11] Patent Number: 5,053,027
[45] Date of Patent: Oct. 1, 1991

[54] FEMALE URINE COLLECTION DEVICE

[76] Inventor: Frank A. Manfredi, 2026 W. 95th St., Cleveland, Ohio 44102

[21] Appl. No.: 515,210

[22] Filed: Apr. 27, 1990

[51] Int. Cl.$^5$ .................... A61M 1/00; A61F 5/44; A61B 5/00
[52] U.S. Cl. .................................... 604/327; 128/761; 604/329; 604/331
[58] Field of Search .............. 604/329, 327, 353; 128/760, 761, 767, 768

[56] References Cited

U.S. PATENT DOCUMENTS

| | | | |
|---|---|---|---|
| 2,815,025 | 12/1957 | Fenton et al. | 128/275 |
| 3,721,243 | 3/1973 | Hesterman et al. | 128/295 |
| 3,724,461 | 4/1973 | Eisenberg | 128/227 |
| 3,749,096 | 7/1973 | Donaldson | 128/293 |
| 3,835,857 | 9/1974 | Rogers, III et al. | 128/295 |
| 3,926,233 | 12/1975 | Brendling | 150/2.5 |
| 4,022,213 | 5/1977 | Stein | 128/295 |
| 4,055,179 | 10/1977 | Manschot et al. | 128/295 |
| 4,073,295 | 2/1978 | Laufbahn | 128/295 |
| 4,202,058 | 5/1980 | Anderson | 4/144.3 |
| 4,270,539 | 6/1981 | Michaud | 128/295 |
| 4,344,432 | 8/1982 | Pankau | 128/275 |
| 4,496,355 | 1/1985 | Hall et al. | 604/327 |
| 4,511,358 | 4/1985 | Johnson, Jr. et al. | 604/353 |
| 4,681,572 | 7/1987 | Tokarz et al. | 128/761 |
| 4,784,654 | 11/1988 | Beecher | 604/329 |
| 4,846,816 | 7/1989 | Manfredi | 604/323 |
| 4,846,817 | 7/1989 | Mohr et al. | 604/329 |
| 4,904,248 | 2/1990 | Vaillancourt | 604/329 |
| 4,955,879 | 9/1990 | Mervine | 604/327 |
| 4,999,550 | 12/1976 | Martin | 128/295 |

OTHER PUBLICATIONS

"Taking Control of Your Life. Introducing the Hollister Female Urinary Incontinence System", brochure–undated.

"Important Instructions for Use of the Misstique EUC System External Urinary Collection System for Women", brochure–Copyright 1985.

*Primary Examiner*—Randall L. Green
*Assistant Examiner*—R. Clarke
*Attorney, Agent, or Firm*—Renner, Otto, Boisselle & Sklar

[57] ABSTRACT

The present invention provides a urine collection device for use by a female having a reservoir for receiving and temporarily collecting urine originating from the female. The reservoir includes a first opening end for insertion within the confines of the labia minor of the female such that the first opening end surrounds the urethral orifice of the female and is positioned between the clitoris and vaginal orifice of the female. The reservoir also includes a second opening end which is spaced from the first opening end and forms a passageway for draining urine from the reservoir. The first opening end of the reservoir is elliptic in shape and includes a protruding rim for forming a seal between the first opening end and the tissue surrounding the urethral orifice of the female. The invention further provides a unique waist belt and urine collection bag for use with the urine collection device.

17 Claims, 2 Drawing Sheets

FEMALE URINE COLLECTION DEVICE

This invention relates to a device for collecting urine from a human. More particularly, the present invention relates to a non-invasive device for collecting urine from a female. The invention further provides a waist belt and urine collection bag for use in conjunction with the urine collection device.

BACKGROUND

The prior art provides various devices for collecting urine from a female. Generally, such devices serve to collect and facilitate the disposal of urine originating from females who are partially or totally incontinent or unable to rid themselves of urine in a normal manner such as through the use of a rest room. Some of these prior art devices are invasive (i.e., they require the insertion of at least a portion of the device into the urethral orifice or the vaginal orifice of the female) while other devices are non-invasive (i.e., they do not require that any portion of the device be inserted into the urethral orifice or the vaginal orifice of the female).

An example of a non-invasive urine collection device for use by a female may be found in Manfredi U.S. Pat. No. 4,846,816. Manfredi discloses a device having a circular opening end which is held in position over the urethral orifice of the female by a waist belt. Another example of a non-invasive device may be found in Michaud U.S. Pat. No. 4,270,539. Michaud discloses a non-invasive device for collecting urine from a female which is held in position by a waist belt. The device includes a pair of circular opening ends that abut the user's body. One of these opening ends is positioned over the vaginal orifice. The other opening end is partially received within the confines of the labia minor of the female and positioned over the urethral opening. The device is intended to be custom fitted or specially made for each user.

SUMMARY OF THE INVENTION

The present invention provides a new and improved non-invasive urine collection device for use by a female. The device provides a fluid tight seal with the user's body and ensures the complete collection of urine emanating or flowing from the female, without the need of custom fitting the device for each specific user. The device, which is designed to be partially inserted within the confines of the labia minor of the female, does not cover or obstruct the vaginal orifice of the female.

In a preferred embodiment the urine collection device includes a reservoir for receiving and temporarily collecting urine originating from the female. The reservoir includes a first opening end for insertion within the confines of the labia minor of the female. The first opening end is elliptic in shape so as to allow the first opening end to more easily conform to the configuration of the cavity created by the female's labia minor. Upon positioning of the first opening end of the device within the confines of the labia minor the first opening end surrounds the urethral orifice of the female and is located between the clitoris and the vaginal orifice of the female. Included along the peripheral edge of the first opening end is a protruding rim which helps to ensure a fluid tight seal between the device and the tissue surrounding the female's urethral orifice.

The reservoir includes a second opening end substantially diametrically opposed to the first opening end. The second opening end forms a conduit or passageway for draining urine from the reservoir. The reservoir also includes a protruding flange located between the first and second opening ends. Disposed along the major surface of the flange closest to the second opening end, and a portion of the reservoir proximate to the second opening end, are sections of hook and loop tape.

The invention further provides an adjustable waist belt for supporting the urine collection device within the confines of the labia minor. The waist belt includes a crotch strap having an elongated opening for receiving the second opening end of the urine collection device. The opening in the crotch strap is elongated so as to allow the adjustment of the position of the urine collection device relative to the crotch strap. Located around the elongated opening in the crotch strap, along the surface of the strap which is in partial contact with the female's body, is a section of hook and loop tape. Upon a user positioning the first opening end of the urine collection device within the confines of her labia minor, and then properly putting on the waist belt and placing the second opening end of the urine collection device through the elongated opening, the hook and loop tape securely engages the hook and loop tape located on the flange and reservoir of the urine collection device, thereby ensuring that the device is held firmly in position relative to the crotch strap and within the confines of the labia minor.

The invention further provides a urine collection bag for use with the urine collection device. The urine collection bag, which is worn on the upper thigh of the user substantially hidden from the public's view, is connected to the urine collection device by a length of flexible tubing.

The foregoing and other features of the invention are hereinafter more fully described and particularly pointed out in the claims, the following description and the annexed drawings setting forth in detail certain illustrative embodiments of the invention, these being indicative, however, of but a few of the various ways in which the principles of the invention may be employed.

DETAILED DESCRIPTION OF PREFERRED EMBODIMENT

Figure 1:
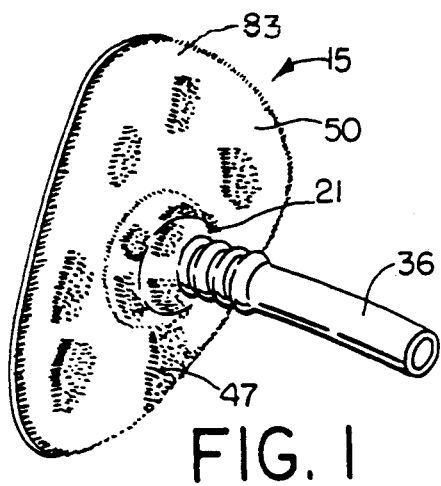
FIG. 1 is a front perspective view of a urine collection device made in accordance with the principles of the present invention.
Figure 2:
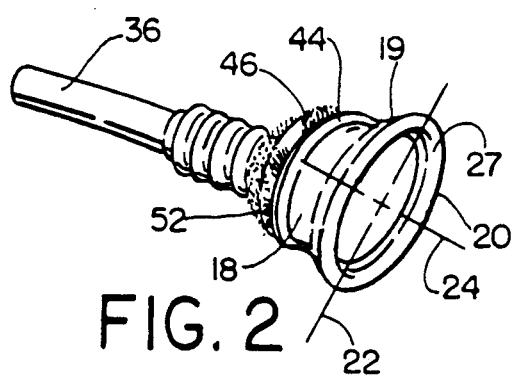
FIG. 2 is a rear perspective view of the urine collection device shown in FIG. 1 with the flange removed.
Figure 3:
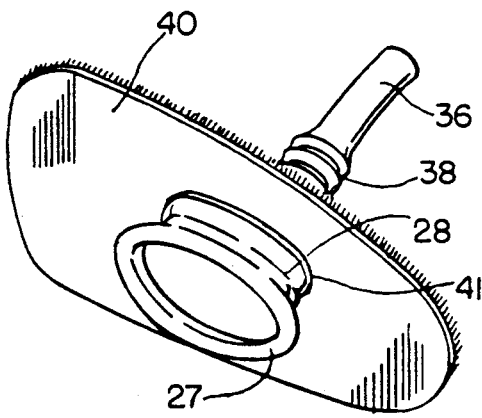
FIG. 3 is a rear perspective view of the urine collection device shown in FIG. 1.

Referring to the drawings and initially to FIGS. 1-3 there is illustrated a female urine collection device 15 made in accordance with the principles of the present invention. Device 15 includes a reservoir 18 forming a hollow cavity for receiving and collecting urine emanating from a female. Reservoir 18 includes a continuous sidewall 19 that generally tapers from a first opening end 20 to a substantially diametrically opposed second opening end 21. Preferably, the thickness of the sidewall 19 is non-uniform such that it is greatest near the second opening end 21 and gradually reduces towards the first opening end 20 so as to provide the area surrounding the first opening end 20 with more flexibility than the area surrounding the second opening end 21. However, care must be taken not to make the sidewall 19 in the area surrounding the first opening end 20 too thin so as to prevent the sidewall 19 from collapsing and closing the first opening end 20 when the urine collection device 15 is utilized by the female.

The first opening end 20 of the device 15 is elliptic in shape. More particularly, the first opening end 20 includes a major diameter designated by line 22 and a minor diameter designated by line 24. The length of the major diameter 22 is greater than the length of the minor diameter 24. Preferably, the length of the major diameter 22 is at least thirty percent greater than the length of the minor diameter 24. Located along the peripheral edge of the first opening end 20 is a protruding rim 27. Also, preferably in the proximity of the protruding rim 27 the sidewall 19 includes a reduced portion 28 wherein the sidewall 19 is substantially concave in cross-section as best seen in FIG. 2.

The second opening end 21 is circular and it serves as a conduit for draining urine from the reservoir 18. Contiguous with the second opening end 21 of the reservoir 18 is a length of flexible hollow tubing 36 having a corrugated portion 38 which allows the length of tubing 36 to flex and bend without closing or obstructing flow through the tube 36.

Positioned between the opening ends 20 and 21, and closest to the second opening end 21, is a removable protruding flange 40 having an elliptic shape opening 41 adapted to receive reservoir 18. Flange 40 is held in position relative to reservoir 18 by a pair of continuous protruding lips 44 extending outwardly from the outer surface of the sidewall 19 of reservoir 18. Lips 44 form a continuous groove 46 which is substantially equal in width to the thickness of the flange 40. The flange 40 is attached to the reservoir 18 by inserting the second opening end 21 of the reservoir 18 into the opening 41 formed in the flange 40 until the flange 40 is located within the confines of the groove 46 formed by lips 44.

Disposed along the front major surface 47 of the flange 40, or the surface of the flange 40 which is closest to second opening end 21 of the reservoir 18 upon attachment of the flange 40 to the reservoir 18, is a section of hook and loop tape 50. Similarly, disposed along the portion of the outer surface of the sidewall 19 of reservoir 18 which surrounds the second opening end 21, between the second opening end 21 and the flange 40, is a section of hook and loop tape 52.

With the exception of the sections of hook and loop tape 50 and 52, urine collection device 15 is preferably produced from a pliable material which becomes more flexible as a result of exposure to the warmth of the human body such as an appropriate grade of latex rubber. Also, preferably the reservoir 18 and the length of flexible tubing 36 are formed as one contiguous piece. Likewise, if desired, the flange 40 and the reservoir 18 may be formed as one contiguous piece. However, by separately producing such pieces a user may dispose of the reservoir 18 and re-use the flange 40. Various manufacturing techniques may be utilized to produce the urine collection device 18 including, for example, extrusion and injection molding techniques.

Figure 5:
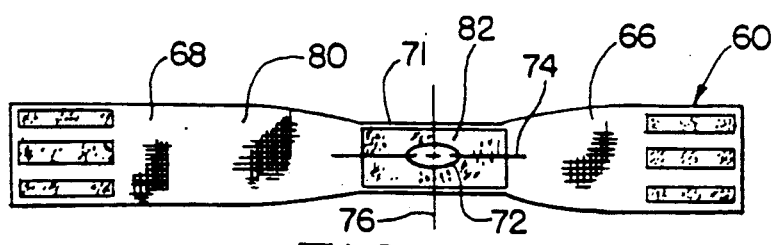
FIG. 5 is a top view of the inner surface of the crotch strap of the waist belt shown in FIG. 4.
Figure 11:
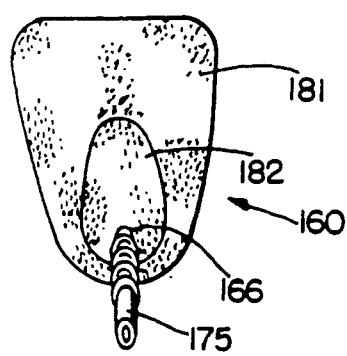
FIG. 11 is a front view of the urine collection device shown in FIG. 10.
Figure 4:
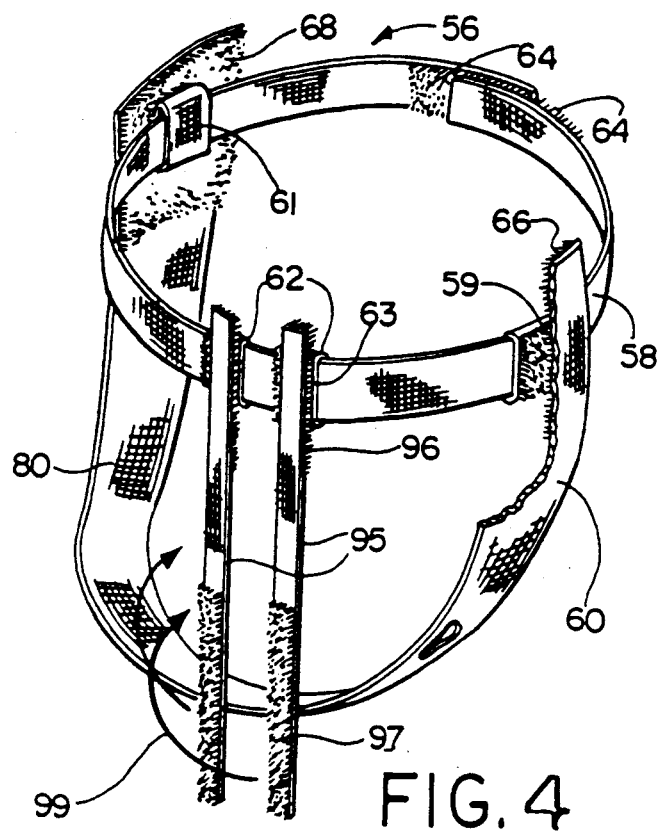
FIG. 4 is a perspective view of an adjustable waist belt for use in connection with the urine collection device shown in FIG. 1.

Referring now to FIGS. 4 and 5 there is illustrated an adjustable waist belt 56 for use in conjunction with urine collection device 15. Waist belt 56 comprises a waist strap 58, a crotch strap 60, a pair of crotch strap supports 61 for engaging the ends of crotch strap 60 and a pair of bag supports 62 for supporting a urine collection bag. Waist strap 58 is formed from a single piece of elastic fabric having disposed at its distal ends sections of hook and loop tape 64 which allow the diameter formed by waist strap 58 to be adjusted.

Crotch strap supports 61 and bag supports 62 are formed from continuous loops of elastic fabric. Waist strap 58 extends freely through the loops formed by crotch strap supports 61 and bag supports 62, thereby allowing crotch strap supports 61 and bag supports 62 to be positioned at various positions along waist strap 58. Included along the forward faces of the crotch strap supports 61 and the bag supports 62 are sections of hook and loop tape 59 and 63 respectively.

Crotch strap 60 is formed from a single piece of elastic fabric and it includes at its distal ends sections of hook and loop tape 66. The sections of hook and loop tape 6 facilitate the attachment of the ends of crotch strap 60 to the sections of hook and loop tape 59 on crotch strap supports 61 at various positions in order to provide for the adjustment of the effective length of crotch strap 60 (i.e., the length of crotch strap 60 extending between crotch strap supports 61 upon the attachment of the ends of the crotch strap 60 to supports 61).

As shown in FIG. 5 crotch strap 60 includes a reduced portion 71 having a smaller width than the front end portion 67 and rear end portion 68 of crotch strap 60. Included within reduced portion 71 and centered towards the front end portion 67 is an opening 72 for receiving and supporting urine collection device 15. Opening 72 is elongated and it includes a major diameter designated by line 74 and a minor diameter designated by line 76. The major diameter 74 is greater in length than the minor diameter 76. Preferably, the major diameter is at least 75 percent greater in length than the length of the minor diameter 76. Disposed along the inner surface 80 of crotch strap 60 in the immediate proximity of opening 72 is a section of hook and loop tape 82.

Figure 7:
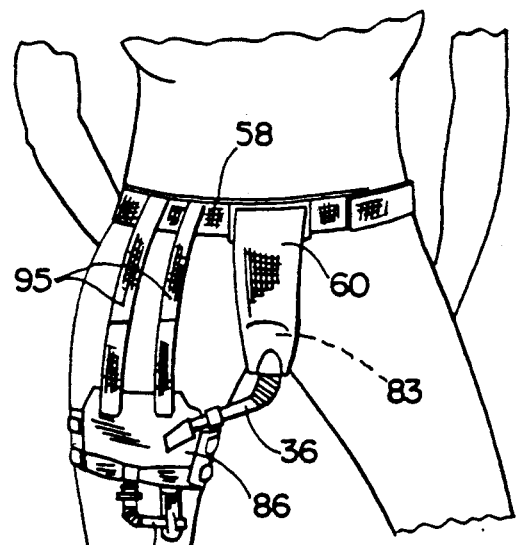
FIG. 7 is a front view of a female wearing the urine collection device shown in FIG. 1, the waist belt shown in FIG. 4 and the urine collection bag shown in FIG. 6.

Urine collection device 15 is utilized by first inserting the first opening end 20 of the device 15 within the confines of the user's labia minor such that the first opening end surrounds the female's urethral orifice and is positioned between the female's clitoris and vaginal orifice and the widest portion 83 of the flange 40 is positioned between the female's urethral orifice and navel as shown in FIG. 7. In this position the major diameter 22 of the first opening end 20 of the reservoir 18 extends substantially perpendicular to the shoulders of the female. Upon insertion of the urine collection device 15 the protruding rim 27 and the reduced portion 2 help to allow the labia minor to grasp and hold onto the urine collection device 15. Protruding rim 27 also increases the surface area of the reservoir 18 which is in contact with the tissue surrounding the urethral orifice thereby helping to promote a seal between the first opening end 20 and the tissue surrounding the urethral orifice.

The elliptic shape of the first opening end 20 is preferred because it substantially replicates the configuration of the cavity formed by a female's labia minor. This elliptic shape is also preferred because it allows a significant amount of forward and backward movement of the device 15 between a female's legs without exposing or failing to cover the female's urethral orifice. Furthermore, this elliptic shape has also been found to minimize the number of urine collection devices 15 having different sized first opening ends 20 that are required to properly service a population of women each of whom have a labia minor that forms a cavity of different size and a urethral orifice with a different spacing between the clitoris and the vaginal orifice.

The female then places the waist strap 58 securely around her waist in the proximity of her navel with the rear end portion 68 of the crotch strap 60 attached to the crotch strap support 61 that is positioned adjacent to the center of the female's lower back. The female then positions the crotch strap 60 between her legs moving the front end portion 67 of the crotch strap 60 towards the other crotch strap support 61 which is positioned near the female's navel. While moving the front end portion 67 of the crotch strap 60 towards the other support 61 the second opening end 21 of the reservoir and the length of tubing 36 are inserted into the elongated opening 72 formed in the crotch strap 60. As the hook and loop tape 66 of the front end portion of the crotch strap 60 engages the hook and loop tape 63 of the crotch strap support 61, the hook and loop tape 82 surrounding the elongated opening 72 securely engages the hook and loop tape 50 of the flange 40 and the hook and loop tape 52 of the reservoir 18.

Once the waist belt 56 and the urine collection device 15 are properly positioned the waist belt 56 serves to help hold the first opening end 20 of the urine collection device 15 securely within the confines of the labia minor while the user moves about. The removal of the urine collection device 15 is easily accomplished by removing the front end portion 67 of the crotch strap 60 from the crotch strap support 61 and down towards the user's knees. As this is done the urine collection device 15 is pulled out of the confines of the labia minor. A user may then remove the waist strap 58 and separate the urine collection device 15 from the crotch strap 60.

Figure 6:
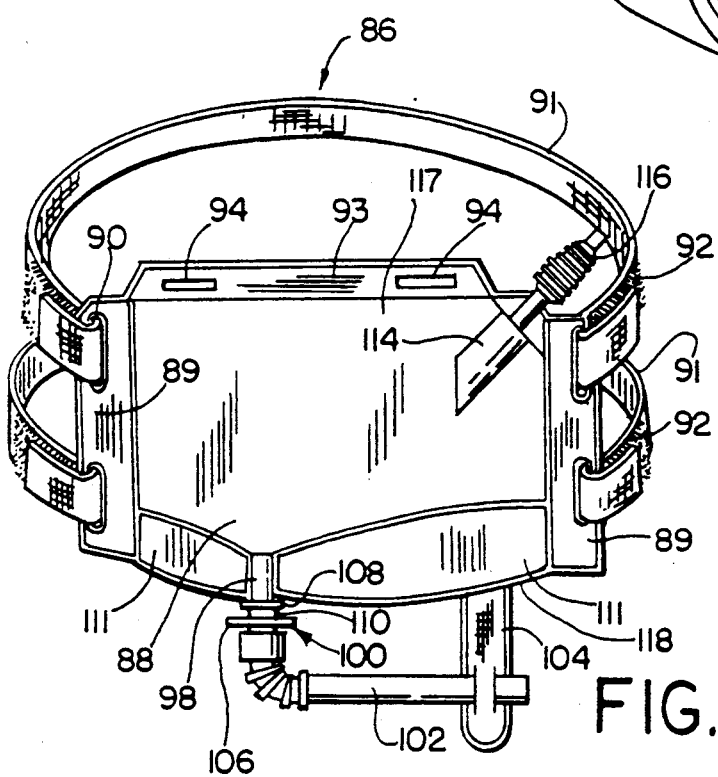
FIG. 6 is a perspective view of a urine collection bag for use with the urine collection device shown in FIG. 1.

Referring now to FIG. 6 there is illustrated a urine collection bag 86 suitable for use with the present invention. Preferably, the major components of bag 86 are produced from a plastic or polymer type material such as pliable nylon or polyethylene. Bag 86 includes an expandable storage chamber 88 that is capable of providing a cavity with an adjustable volume that expands as urine flows into the chamber 88 and collapses as urine is drained from the chamber 88. Preferably, chamber 88 is square in shape. More preferably, as shown in FIG. 6 chamber 88 is rectangular in shape having its major length extending perpendicular to the user's leg. Disposed along the lateral edges of chamber 88 are protruding flanges 89 having a pair of slots 90 formed therein. Slots 90 are adapted to receive leg straps 91 which are formed from elastic fabric and include sections of hook and loop tape 92 mounted at their distal ends to facilitate the adjustment of the lengths of the leg straps 91. Preferably, the backside of bag 86 (i.e., the side of the bag 86 that is contiguous with the user's leg) includes a fabric outer covering such that a user is not subjected to the discomfort that may result from a large area of plastic type material being in contact with the human skin.

Applicant has found that the use of the flanges 89 that extend along substantially the entire vertical length of chamber 88 tends to distribute the force imparted upon chamber 88 by leg straps 91 as straps 91 are secured around the user's leg, thereby helping to prevent chamber 88 from collapsing and restricting the free flow of urine throughout chamber 88. Chamber 88 also includes a flange 93 extending along the top of chamber 88 having two slots 94 to facilitate the attachment of bag straps 95. Bag straps 95 are formed from an elastic fabric and include sections of hook and loop tape 96 and 97 at their distal ends to facilitate the attachment of the bag straps 95 to the top flange 93 and the bag supports 62.

Formed in the bottom of the chamber 88 is a drain opening 98 including a valve 100. Attached to the valve 100 is a length of hollow flexible tubing 102 which is held in position by a flexible strap 104 which is formed along the bottom of chamber 88. Flexible tubing 102 assists a user in draining chamber 88 by allowing a user to control and direct the flow of urine emanating from bag 88 when valve 100 is opened. Valve 100 is opened by exerting an upward force upon the bottom flange 106 and moving it toward the top flange 108. The stem 110 of valve 100 is biased by a spring such that upon releasing bottom flange 106, the bottom flange 106 is pushed away from top flange 108 thereby biasing valve 100 in the closed position. Preferably, valve 100 is of the same construction as the check valve disclosed in Manfredi U.S. Pat. No. 4,846,816.

As shown in FIG. 6, chamber 88 includes along its bottom portion a pair of heat sealed areas 111 that are curved towards opening 98 formed in chamber 88 thereby forming a curved bottom for chamber 88 that slopes towards opening 98. This particular configuration helps to ensure more complete draining of chamber 88 when valve 100 is opened and it also helps to prevent chamber 88 from collapsing and blocking opening 98.

Formed at the top of chamber 88 is an intake opening 114 having a nipple 116 with a corrugated flexible portion 117 inserted therein. Nipple 116 facilitates the releasable attachment of the length of tubing 36 extending from reservoir 18. Preferably, intake opening 114 is formed from and along the front wall 117 of chamber 88 at about a 45° angle relative to the straight bottom edge 118 of bag 86 or the major length of the user's leg. By forming the intake opening 114 on this angle the degree of bend required by the length of tubing 36 extending from reservoir 18 is minimized thereby helping to prevent the length of tubing 36 from pulling upon the reservoir 18. Furthermore, by forming the opening 114 out of the front wall 117 of chamber 88, the possibility of the flow of urine into chamber 88 becoming restricted has been found to be minimized.

As shown in FIG. 7, collection bag 86 is worn upon the top of the user's thigh in the proximity of the urine collection device 15. Collection bag 86 is easily attached to waist belt 56 by first looping the distal ends of straps 95 through the respective slots 94 and doubling the distal ends back (as indicated by arrow 99 in FIG. 4) such that the sections of hook and loop tape 97 engage themselves at the desired position thereby allowing a user to adjustably position the opening 98 in chamber 88 below the second opening end 21 in reservoir 18. The proximate ends of strap 95 are then attached to bag supports 62 such that sections of hook and loop tape 96 on straps 95 engage sections of hook and loop tape 63 on bag supports 62. Straps 91 are then secured around the user's leg thereby completing the mounting of collection bag 88. Collection bag 86 provides a distinct advantage because its major length does not extend to any substantial degree down the user's leg thereby helping a user to wear the collection bag 86 underneath a dress or loose fitting pants substantially hidden from the view of the general public.

Figure 9:
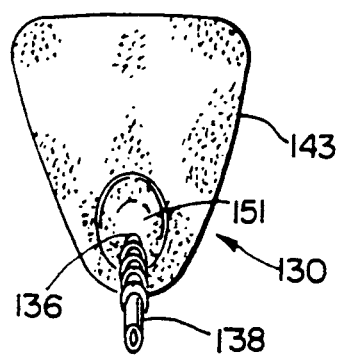
FIG. 9 is a front view of the urine collection device shown in FIG. 8.
Figure 8:
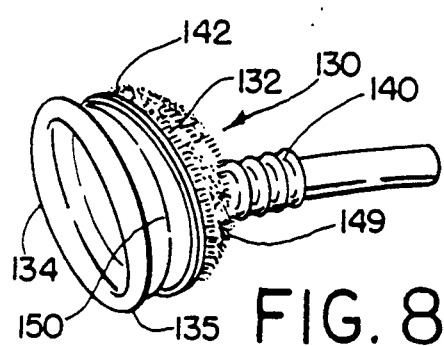
FIG. 8 is a rear perspective view of an alternative embodiment of a urine collection device made in accordance with the principles of the present invention with the flange removed.

Referring now to FIGS. 8 and 9 there is illustrated another embodiment of a urine collection device 130 made in accordance with the principles of the present invention. Like the previously illustrated embodiment, urine collection device 130 includes a reservoir 132 having an elliptic shape first opening end 134 having a protruding peripheral rim 135. Reservoir 132 also includes a second opening end 136 for draining the urine from reservoir 132. Contiguous with the second opening end 136 is a length of flexible tubing 138 having a corrugated portion 140.

As with urine collection device 15, urine collection device 130 includes a continuous groove 142 for receiving a flange 143 formed along the outside diameter of the reservoir 132. Reservoir 132 includes a substantially spherical portion 148 located between the groove 142 and the second opening end 136. Spherical portion 148 is preferred for use with those females who expel a large amount of urine over a short period of time, spherical portion 148 serving as a temporary holding tank a urine drains out of the reservoir 132.

Located between the groove 142 and the first opening end 134 is a substantially cylindrical shape portion 149. Preferably, the thickness of the sidewall of the cylindrical shape portion 149 is significantly less than the thickness of the sidewall of the spherical shape portion 148 so as to allow the cylindrical shape portion 149 to be more pliable and thus better able to adapt to the confines of the user's labia minor. Also, preferably the cylindrical shape portion 149 includes a reduced portion 150 wherein the sidewall is substantially concave in cross-section which along with the protruding rim 134 helps to ensure relocation of a portion of the device 130 within the female's labia minor.

In urine collection device 130 the second opening end 136 is located near the bottom of the reservoir 132. This particular configuration is preferred for users who are bedridden or unable to stand up for it helps to ensure that the urine is completely drained out of the reservoir 132 and away from the user. Included along the outer surface of spherical portion 148 is a section of hook and loop tape 151 which helps to hold the urine collection device 130 in position relative to crotch strap 60 upon insertion of the second opening end 136 of the device 130 into the elongated opening 72 formed in crotch strap 60.

Figure 10:
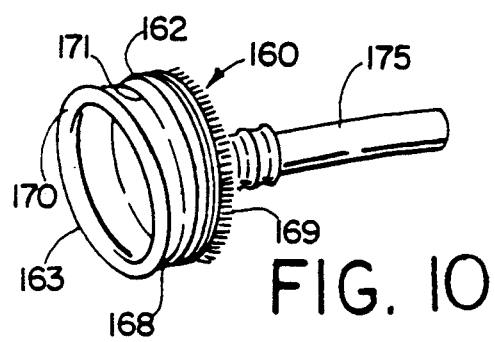
FIG. 10 is a rear perspective view of another embodiment of a urine collection device made in accordance with the principles of the present invention with the flange removed.

Referring now to FIGS. 9 and 10 there is illustrated yet another embodiment of a urine collection device 160 made in accordance with the principles of the present invention. Device 160 includes a reservoir 162 having an elliptic shape first opening end 163. Like the previously illustrated urine collection device 130, urine collection device 160 includes a second opening end 166 disposed along the bottom of the somewhat cylindrical shaped reservoir 162 formed by the upstanding or substantially straight continuous sidewall 168 and end wall 169. Included along the end of sidewall 168 is a protruding peripheral rim 170. Preferably, sidewall 168 is of a reduced thickness as compared to end wall 169 so as to allow sidewall 168 to be more flexible and pliable and thus more capable of adapting to the confines of the user's labia minor. Also, preferably sidewall 168 includes a reduced portion 171 wherein the sidewall is substantially concave in cross-section.

Contiguous with the second opening end 166 is length of hollow flexible tubing 175. Formed along the outer diameter of reservoir 162 is a continuous groove 180 adapted to receive a flange 181 which is substantially similar to flanges 40 and 143 noted above. Provided along the outer surface of end wall 169 is a section of hook and loop tape 182 which helps to hold urine collection device 160 in position relative to crotch strap 60 upon insertion of the length of tubing 175 into opening 72 formed in crotch strap 60.

Although the invention has been shown and described with respect to certain preferred embodiments, it is obvious that equivalent alterations and modifications will occur to others skilled in the art upon the reading and understanding of the specification. The present invention includes all such equivalent alterations and modifications, and is limited by the scope of the following claims.

I claim:

1. A waist belt for supporting a urine collection device in contact with a user's body comprising:

a waist strap for encircling such user's waist;

a crotch strap for attachment to the waist strap, said crotch strap having an opening therein adapted to receive a portion of such urine collection device, said opening in said crotch strap being elongated such that it has a minor diameter extending substantially parallel to the shoulders of such user and a major diameter extending substantially perpendicular to the shoulders of such user, said major diameter having a length substantially greater than the length of said minor diameter;

said crotch strap including a pair of crotch strap supports including loops through which said waist strap freely extends so as to allow the adjustable positioning of said crotch strap supports upon said waist strap, said crotch strap supports including a first section of hook and loop tape to engage a second section of hook and loop tape disposed along the distal ends of said crotch strap; and said waist strap including sections of hook and loop tape disposed at the distal ends of said waist strap to facilitate the adjustment of the diameter formed by said waist strap.

2. A waist belt as set forth in claim 1 wherein said crotch strap in the proximity of said elongated opening includes a section of hook and loop tape.

3. A waist belt as set forth in claim 1 wherein said crotch strap in the proximity of said elongated opening includes a narrowed portion of reduced width.

4. A waist belt as set forth in claim 1 including at least one urine collection bag support to facilitate the attachment of a urine collection bag.

5. A waist belt as set forth in claim 4 wherein said bag support forms a loop for freely receiving said waist strap thereby allowing said bag support to be positioned at various locations along with waist strap.

6. A urine collection assembly for use by a female comprising:

a urine collection device comprising a reservoir for partial insertion within the confines of the labia minor of such female;

a urine collection bag having a chamber for receiving and storing urine collected by said urine collection device;

a waist belt for supporting said urine collection device upon such female's body, said waist belt having a crotch strap for positioning between the legs of such female having an opening therein adapted to receive a portion of said urine collection device, said opening in said crotch strap being elongated such that it has a minor diameter extending substantially parallel to the shoulders of such female and a major diameter extending substantially perpendicular to the shoulders of such female, said major diameter having a length substantially greater than the length of said minor diameter such that prior to the insertion of said urine collection device into said opening in said crotch strap the position of said urine collection device may be adjusted relative to the major length of said crotch strap;

said reservoir of said urine collection device including a first opening end for insertion within the confines of the labia minor of such female such that said first opening end surrounds the urethral orifice of such female and is positioned between the clitoris and vaginal opening of such female, and a second opening end spaced from said first opening end forming a conduit for draining urine from said reservoir, said major diameter of said first opening end being at least thirty percent greater in length than said minor diameter of said first opening end; and said chamber of said urine collection bag including an intake opening formed in the forward wall of said chamber at about a 45° angle relative to a line extending perpendicular to the major length of such female's leg.

7. A urine collection bag for use upon a user's leg in connection with a urine collection device, said urine collection bag including a chamber having an intake opening disposed near the top of said chamber and a drain opening disposed along the bottom of said chamber, said intake opening formed from a wall of said chamber and extending at an angle relative to the major length of such user's leg, said intake opening extending at about a 45° angle relative to the major length of such user's leg.

8. A urine collection assembly for use by a female comprising:

a urine collection device;

a waist belt for supporting said urine collection device upon such female's body; and a urine collection bag for use upon such female's leg, said urine collection bag including a chamber having an intake opening disposed near the top of said chamber, said intake opening formed from a wall of said chamber and extending at about a 45° angle relative to the major length of such female's leg.

9. A urine collection assembly for use by a female as set fort in claim 8 wherein said urine collection device includes a reservoir for receiving and temporarily collecting urine originating from such female having a first opening end for partial insertion within the confines of the labia minor of such female such that said first opening end surrounds the urethral orifice of such female and is positioned between the clitoris and vaginal orifice of such female, and a second opening end spaced from said first opening end that forms a passageway for draining urine from said reservoir, said first opening end being elliptic in shape and having a protruding peripheral rim for forming a seal between said first opening end and the tissue surrounding the urethral orifice of such female.

10. A urine collection assembly as set forth in claim 8 wherein said device includes a flange protruding from said reservoir, said flange being positioned between said first opening end and said second opening end.

11. A urine collection assembly as set forth in claim 10 wherein said flange includes a section of hook and loop tape disposed along at least a portion of one of its major surfaces.

12. A urine collection assembly as set forth in claim 10 wherein said reservoir includes a spherical shaped portion and said second opening end is located along the bottom of said spherical shaped portion.

13. A urine collection assembly as set forth in claim 10 wherein said reservoir is substantially cylindrical in shape and said second opening end is located along the bottom of said reservoir.

14. A urine collection assembly as set forth in claim 10 wherein said second opening end of said reservoir includes a length of tube attached thereto and said reservoir in the proximity of said protruding peripheral rim includes a reduced portion formed by a substantially concave sidewall.

15. A urine collection assembly as set forth in claim 14 wherein said tube includes a corrugated portion so as to help allow said tube to freely bend.

16. A urine collection assembly as set forth in claim 14 wherein said flange is releasably connected to said reservoir.

17. A urine collection assembly as set forth in claim 16 wherein said reservoir includes a continuous groove formed thereon for releasably engaging said flange.

* * * * *